United States Patent
Yang et al.

(10) Patent No.: US 11,505,570 B2
(45) Date of Patent: Nov. 22, 2022

(54) ORGANIC ACID SALT OF NICOTINAMIDE RIBOSIDE, COMPOSITION INCLUDING ORGANIC ACID SALT, AND PREPARATION METHODS OF ORGANIC ACID SALT AND COMPOSITION

(71) Applicant: SHENZHEN DIECKMANN TECH CO., LTD, Shenzhen (CN)

(72) Inventors: Chaowen Yang, Shenzhen (CN); Lei Wang, Shenzhen (CN); Jialiang Song, Shenzhen (CN); Dingliang Fu, Shenzhen (CN)

(73) Assignee: SHENZHEN DIECKMANN TECH CO., LTD, Shenzhen (CN)

( * ) Notice: Subject to any disclaimer, the term of this patent is extended or adjusted under 35 U.S.C. 154(b) by 0 days.

(21) Appl. No.: 17/595,192

(22) PCT Filed: May 11, 2020

(86) PCT No.: PCT/CN2020/089566
§ 371 (c)(1),
(2) Date: Nov. 10, 2021

(87) PCT Pub. No.: WO2021/196349
PCT Pub. Date: Oct. 7, 2021

(65) Prior Publication Data
US 2022/0204543 A1 Jun. 30, 2022

(30) Foreign Application Priority Data
Apr. 3, 2020 (CN) .......................... 202010258334.4

(51) Int. Cl.
C07H 19/048 (2006.01)
A61K 47/38 (2006.01)
A61K 47/46 (2006.01)

(52) U.S. Cl.
CPC .......... *C07H 19/048* (2013.01); *A61K 47/38* (2013.01); *A61K 47/46* (2013.01)

(58) Field of Classification Search
CPC .................................. A61K 47/38; A61K 47/46
See application file for complete search history.

(56) References Cited

U.S. PATENT DOCUMENTS

| | | | |
|---|---|---|---|
| 2017/0121746 A1* | 5/2017 | Velasquez | C12P 19/28 |
| 2018/0362570 A1 | 12/2018 | Ganapati et al. | |

FOREIGN PATENT DOCUMENTS

| | | |
|---|---|---|
| CN | 105873937 A | 8/2016 |
| CN | 106536535 A | 3/2017 |
| CN | 106715455 A | 5/2017 |
| CN | 108774278 A | 11/2018 |
| WO | 2019126482 A1 | 6/2019 |
| WO | 2019210607 A1 | 11/2019 |
| WO | 2019226755 A1 | 11/2019 |

OTHER PUBLICATIONS

Ricardo Alvarez, et al. Nicotinamide Riboside Derivatives: Single Crystal Growth and Determination of X-ray Structures, Crystal Growth & Design, 2019, pp. 4019-4028, vol. 19.

* cited by examiner

*Primary Examiner* — Genevieve S Alley
(74) *Attorney, Agent, or Firm* — Bayramoglu Law Offices LLC

(57) ABSTRACT

An organic acid salt of nicotinamide riboside (NR) is provided, where an organic acid is selected from the group consisting of malic acid, citric acid, royal jelly acid, and the like, and a molar ratio of the NR to the organic acid is 1:2 or 1:1. A compound composition of an organic acid salt of NR and a carrier is further provided, where the carrier is selected from the group consisting of niacin, glutamic acid, royal jelly acid, nervonic acid, microcrystalline cellulose (MCC), and apple cider vinegar powder. The present disclosure adopts an organic acid with strong acidity, and such an organic acid can form an intimate ion pair with NR and show some hydrophobicity, which improves the stability of NR. The carrier can prevent moisture penetration and improve the water resistance of the organic acid salt.

8 Claims, No Drawings

ORGANIC ACID SALT OF NICOTINAMIDE RIBOSIDE, COMPOSITION INCLUDING ORGANIC ACID SALT, AND PREPARATION METHODS OF ORGANIC ACID SALT AND COMPOSITION

CROSS REFERENCE TO THE RELATED APPLICATIONS

This application is the national phase entry of International Application No. PCT/CN2020/089566, filed on May 11, 2020, which is based upon and claims priority to Chinese Patent Application No. 202010258334.4, filed on Apr. 3, 2020, the entire contents of which are incorporated herein by reference.

TECHNICAL FIELD

The present disclosure belongs to the technical field of medicine, and specifically relates to an organic acid salt of nicotinamide riboside (NR), a composition including the organic acid salt, and preparation methods of the organic acid salt and the composition.

BACKGROUND

NR is a derivative of vitamin B3 (also known as niacin). A large number of studies have shown that NR has the functions of enhancing the metabolism of an organism, preventing the aging of stem cells, maintaining the functions of stem cells, and the like. Liver cancer research results have shown that the dietary supplementation of NR can prevent the development of liver cancer in mice and induce tumor regression, which shows no side effects at a high dosage. In addition, β-nicotinamide mononucleotide (β-NMN) obtained through phosphorylation of β-nicotinamide ribose (β-NR) is a synthetic substrate of coenzyme I in organisms. Studies have shown that β-NMN has the activities of antiaging, regulating insulin secretion, and affecting an mRNA expression level. Therefore, β-NR and β-NMN have become hot compounds in the fields of drug development, regenerative medicine, and skin care, which have promising market demand prospects.

NR can freely exist in the form of a cation (formula I), which is unstable and needs to form an ion pair (structure II) with an anion to be stable.

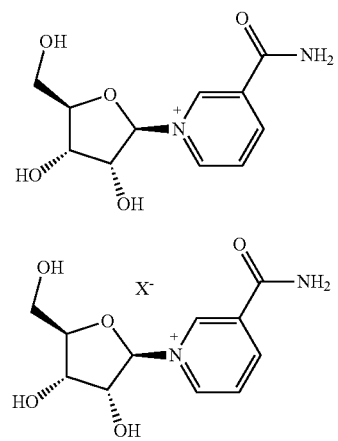

A chloride salt of NR has been reported in a literature, but is still not very stable, particularly sensitive to water, light, and temperature. Therefore, in order to facilitate the use of NR and expand a use scope of NR, it is necessary to study a more stable form of NR. In addition, NR is currently used in a relatively single mode and cannot play a complementary role with other compounds.

SUMMARY

A first objective of the present disclosure is to provide a novel organic acid salt of NR that can exist stably.

A second objective of the present disclosure is to provide a preparation method of the organic acid salt of NR.

A third objective of the present disclosure is to provide a composition including organic acid salt of NR.

A fourth objective of the present disclosure is to provide a preparation method of the composition.

In order to achieve the above objectives, the present disclosure adopts the following technical solutions.

The present disclosure provides an organic acid salt of NR, where an organic acid is selected from the group consisting of malic acid, tannic acid, eicosapentaenoic acid (EPA), docosahexaenoic acid (DHA), caffeic acid, trans-cinnamic acid, trans-4-hydroxy-cinnamic acid, monosodium citrate, disodium citrate, citric acid, chlorogenic acid, gluconic acid, ferulic acid, royal jelly acid, nervonic acid, chicoric acid, rosmarinic acid, carnosic acid, niacin, adipic acid, lauric acid, salicylic acid, monopotassium glycyrrhizinate (MPG), folic acid, chondroitin sulfate (CS), potassium hydrogen tartrate, glutamic acid, and aspartic acid.

The above organic acids each have at least one free carboxyl group and are in a solid state at room temperature.

Further, a molar ratio of the NR to the organic acid may be 1:2.

Further, a molar ratio of the NR to the organic acid may be 1:1.

Further, the organic acid may be citric acid, malic acid, or royal jelly acid.

The present disclosure also provides a preparation method of the organic acid salt of NR, including: under the protection of nitrogen, dissolving NR in methanol, adding an organic acid, and stirring a resulting mixture; adding methyl tert-butyl ether (MTBE) or ethyl acetate, and further stirring; and filtering, washing, and drying to obtain a product.

The present disclosure also provides a composition of an organic acid salt of NR, including organic acid salt of NR and a carrier, where the carrier is selected from the group consisting of malic acid, tannic acid, EPA, DHA, caffeic acid, trans-cinnamic acid, trans-4-hydroxy-cinnamic acid, lactic acid, monosodium citrate, disodium citrate, citric acid, chlorogenic acid, gluconic acid, ferulic acid, royal jelly acid, nervonic acid, chicoric acid, rosmarinic acid, carnosic acid, niacin, adipic acid, lauric acid, MPG, folic acid, CS, potassium hydrogen tartrate, salicylic acid, glycine, glutamic acid, alanine, arginine, leucine, isoleucine, valine, cystine, cysteine, methionine, threonine, serine, phenylalanine, tyrosine, tryptophan, proline, hydroxyproline, and aspartic acid; the organic acid salt is the organic acid salt described above; and a molar ratio of the NR to the organic acid is 1:2 or 1:1.

Further, the carrier may be selected from the group consisting of niacin, glutamic acid, royal jelly acid, and nervonic acid.

Further, the organic acid salt may be a malate of NR.

Further, a molar ratio of the organic acid salt of NR to the carrier may be 1:1.

The present disclosure also provides a composition of an organic acid salt of NR, including organic acid salt of NR and a carrier, where the carrier is selected from the group consisting of microcrystalline cellulose (MCC) and apple cider vinegar powder; the organic acid salt is the organic acid salt described above; and a molar ratio of the NR to the organic acid is 1:2 or 1:1.

Further, the organic acid salt may be selected from the group consisting of a malate and citrate of NR.

Further, a mass ratio of the organic acid salt of NR to the carrier may be 1:1.

The present disclosure also provides a preparation method of the composition of an organic acid salt of NR, including: under the protection of nitrogen, mixing and grinding an organic acid salt of NR and a carrier.

The present disclosure has the following beneficial effects.

1. The organic acid salt of NR of the present disclosure adopts an organic acid with strong acidity, and such an organic acid has a free carboxyl group, which can provide a lone paired electron to form an intimate ion pair with a nitrogen cation of NR and lead to some hydrophobicity. The hydrophobicity results in a very prominent stabilization effect on NR and improves the stability of the organic acid salt of NR.

2. When NR and an organic acid are present in a molar ratio of 1:2, one molecule of the NR and two molecules of the organic acid can exist stably. One molecule of the organic acid forms an ion pair with the NR, and then the other molecule of the organic acid forms a hydrogen bond with basic amide in the NR due to acid-base interaction, thereby achieving acid-base pairing, which further improves the stability of the organic acid salt of NR.

3. The organic acid salt of NR is compounded with MCC. The MCC has hydrophobicity and heat resistance, which can prevent moisture penetration and improve the water resistance of the organic acid salt.

4. NR can be converted into nicotinamide adenine dinucleotide ($NAD^+$, also known as coenzyme I) capable of transferring protons in the organism. $NAD^+$ participates in physiological reactions such as energy metabolism, ATP synthesis, DNA repair, cell apoptosis inhibition, and decomposition of proteins, carbohydrates, and fats in an organism. In the present disclosure, an organic acid and apple cider vinegar powder that can participate in the above-mentioned metabolism and other physiological activities are selected and compounded with NR to form a composite nutritional additive, and the components can be complementary and coordinated to produce a superimposed effect. Tests have confirmed that the addition of an organic acid and apple cider vinegar powder as a carrier does not significantly affect the stability of the organic acid salt of NR, and this composite nutritional additive has potential application value.

DETAILED DESCRIPTION OF THE EMBODIMENTS

The present disclosure is further described below with reference to specific examples. The parts below all refer to parts by weight.

EXAMPLE 1

Preparation of a citrate of NR (1:1)

Under the protection of nitrogen and at a temperature of −10° C. to −5° C., NR (0.0220 mol, 1 eq) was dissolved in 60 mL of methanol, then anhydrous citric acid (0.0264 mol, 1.2 eq) was added, and a resulting mixture was stirred for 2 h; and then 75 mL of anhydrous MTBE was added, and a resulting mixture was further stirred for 30 min, filtered under the protection of nitrogen, rinsed with anhydrous diethyl ether, and dried at a temperature below −5° C. to obtain a product (0.0123 mol). In the product (NRX), a molar ratio of NR to citric acid (X) was 1:1; and a yield was 55.91%.

Characterization data:

HNMR(400 MHz,MeOD):δ9.72 (s,1H), 9.42-9.43 (d,1H), 9.01-9.03 (d,1H), 8.25-8.30 (m,1H), 6.18-6.19 (d,1H), 4.42-4.464 (m,2H), 4.30-4.32 (t,1H), 4.01-4.05 (dd, 1H), 3.85-3.89 (dd,1H), 2.67-2.79 (q,4H);

MS(ESI+):254.96[M-1],MS(ESI−): 191.12[M-1];

IR (KBr) $v_{max}$ 3412, 2940, 2375, 1692, 1612, 1516, 1395, 1232, 1098, 894, 677, 622 $cm^{-1}$.

EXAMPLE 2

Preparation of a citrate of NR (1:2)

Under the protection of nitrogen and at a temperature of −10° C. to −5° C., NR (0.0220 mol, 1 eq) was dissolved in 60 mL of methanol, then anhydrous citric acid (0.0495 mol, 2.25 eq) was added, and a resulting mixture was stirred for 2 h; and then 150 mL of anhydrous MTBE was added, and a resulting mixture was further stirred for 30 min, filtered under the protection of nitrogen, rinsed with anhydrous diethyl ether, and dried at a temperature below −5° C. to obtain a product (0.0125 mol). In the product ($NRX_2$), a molar ratio of NR to citric acid (X) was 1:2; and a yield was 56.82%.

Characterization data:

HNMR(400 MHz,MeOD):δ9.73 (s,1H), 9.43-9.45 (d,1H), 9.04-9.06 (d,1H), 8.27-8.32 (m,1H), 6.20-6.21 (d,1H), 4.43-4.45 (m,2H), 4.30-4.33 (t,1H), 4.02-4.05 (d,1H), 3.85-3.89 (d,1H), 2.74-2.86 (q,8H);

MS(ESI+):254.97[M-1],MS(ESI−): 191.16[M-1];

IR (KBr) $v_{max}$ 3425, 2929, 2370, 1697, 1624, 1516, 1394, 1219, 1097, 893, 678, 623 $cm^{-1}$.

When the NR and the anhydrous citric acid were fed in a molar ratio of 1:3.3, characterization data of an obtained product were the same, indicating that the product was a product ($NRX_2$) in which a molar ratio of NR to citric acid (X) was 1:2.

EXAMPLE 3

Preparation of a malate of NR (1:1)

Under the protection of nitrogen and at a temperature of −10° C. to −5° C., NR (0.0195 mol, 1 eq) was dissolved in 60 mL of methanol, then anhydrous malic acid (0.0234 mol, 1.2 eq) was added, and a resulting mixture was stirred for 2 h; and then 100 mL of anhydrous MTBE was added, and a resulting mixture was further stirred for 30 min, filtered under the protection of nitrogen, rinsed with anhydrous diethyl ether, and dried at a temperature below −5° C. to obtain a product (0.01334 mol). In the product (NRX), a molar ratio of NR to malic acid (X) was 1:1; and a yield was 57%.

Characterization data:

HNMR(400 MHz,MeOD): δ9.72 (s,1H), 9.42-9.44 (d,1H), 9.02-9.04 (d,1H), 8.25-8.29 (t,1H), 6.18-6.19 (d,1H), 4.41-4.44 (m,2H), 4.26-4.30 (m,2H), 3.99-4.03 (dd, 1H), 3.83-3.87 (dd,1H), 2.49-2.80 (dd,2H);

MS(ESI+):254.96[M-1],MS(ESI−):133.04[M-1];

IR (KBr) $v_{max}$3379, 2937, 1691, 591, 1100, 677, 6 cm⁻.

EXAMPLE 4

Preparation of a malate of NR (1:2)

Under the protection of nitrogen and at a temperature of −10° C. to −5° C., NR (0.0195 mol, 1 eq) was dissolved in 45 mL of methanol, then anhydrous malic acid (0.043875 mol, 2.25 eq) was added, and a resulting mixture was stirred for 2 h; and then 80 mL of anhydrous MTBE was added, and a resulting mixture was further stirred for 30 min, filtered under the protection of nitrogen, rinsed with anhydrous diethyl ether, and dried at a temperature below −5° C. to obtain a product (0.0118 mol). In the product (NRX$_2$), a molar ratio of NR to malic acid (X) was 1:2; and a yield was 60.51%.

Characterization data:

HNMR(400 MHz,MeOD): δ9.73(s,1H), 9.43-9.45 (d,1H), 9.04-9.06 (d,1H), 8.27-8.31 (m,1H), 6.19-6.20 (d,1H), 4.43-4.45 (m,2H), 4.31-4.34 (m,3H), 4.01-4.05 (dd, 1H), 3.85-3.89 (dd,1H), 2.53-2.83 (dd,4H);

MS(ESI+):254.94[M-],MS(ESI−):133.03[M-1];

IR (KBr) $v_{max}$3409, 2940, 1698, 1580, 1411, 1293, 1181, 1098, 1028, 658 cm⁻¹.

When the NR and the anhydrous malic acid were fed in a molar ratio of 1:3.3, characterization data of an obtained product were the same, indicating that the product was a product (NRX$_2$) in which a molar ratio of NR to malic acid (X) was 1:2.

EXAMPLE 5

Preparation of a royal jelly acid salt of NR (1:2)

Under the protection of nitrogen and at a temperature of −10° C. to −5° C., NR (0.0400 mol, 1 eq) was dissolved in 60 mL of methanol, then royal jelly acid (0.0860 mol, 2.15 eq) was added, and a resulting mixture was stirred for 2 h; and then 120 mL of anhydrous ethyl acetate was slowly added, and a resulting mixture was further stirred for 30 min, filtered under the protection of nitrogen, rinsed with anhydrous diethyl ether, and dried at a temperature below −5° C. to obtain 12.5 g of a product (0.02 mol). In the product (NRX$_2$), a molar ratio of NR to royal jelly acid (X) was 1:2; and a yield was 50%.

Characterization data:

HNMR(400 MHz,MeOD): δ9.73 (s,1H), 9.44 (s,1H), 9.04-9.05 (d,1H), 8.30 (m,1H), 6.58-6.66 (m,2H), 6.18 (m,1H), 5.81-5.85 (d,2H), 4.92 (m,2H), 4.31-4.43 (t,1H), 3.85-4.05 (dd,2H), 3.54-3.57 (t,4H), 2.13-2.18 (m,4H), 1.51-1.56 (m,4H), 1.45-1.49 (m,4H), 1.37 (m,12H);

MS(ESI+):254.96[M-],MS(ESI−): 185.23[M-1];

IR (KBr) $v_{max}$3384, 2924, 1705, 1654, 1555, 1421, 1389, 1187, 1098, 1053, 977, 869, 677 cm⁻¹.

EXAMPLE 6

Preparation of a malate of NR with niacin as a carrier

Under the protection of nitrogen, 0.01 mol of the malate of NR in Example 4 was added to 0.01 mol of niacin, and a resulting mixture was ground at a low temperature (about 16° C., the same below) for about 10 min until the mixture had a particle size of about 200 mesh to obtain 6.4 g of a mixture of malate and nicotinate of NR.

IR (KBr) $v_{max}$3409, 2927, 1695, 1584, 1398, 1319, 1101, 1028, 747, 677, 636 cm⁻¹.

EXAMPLE 7

Preparation of a malate of NR with glutamic acid as a carrier

Under the protection of nitrogen, 0.01 mol of the malate of NR in Example 4 was added to 0.01 mol of glutamic acid, and a resulting mixture was ground at a low temperature for about 10 min until the mixture had a particle size of about 200 mesh to obtain 6.65 g of a mixture of malate and glutamate of NR.

IR (KBr) $v_{max}$3415, 2937, 1692, 1593, 1404, 1092, 1028, 670 cm⁻¹.

EXAMPLE 8

Preparation of a malate of NR with royal jelly acid as a carrier

Under the protection of nitrogen, 0.01 mol of the malate of NR in Example 4 was added to 0.01 mol of royal jelly acid, and a resulting mixture was ground at a low temperature for about 10 min until the mixture had a particle size of about 200 mesh to obtain 7.05 g of a mixture of malate and royal jelly acid salt of NR.

IR (KBr) $v_{max}$3437, 2934, 1698, 1651, 1401, 1095, 684 cm⁻¹.

EXAMPLE 9

Preparation of a malate of NR with nervonic acid as a carrier

Under the protection of nitrogen, 0.01 mol of the malate of NR in Example 4 was added to 0.01 mol of nervonic acid, and a resulting mixture was ground at a low temperature for about 10 min until the mixture had a particle size of about 200 mesh to obtain 8.85 g of a mixture of malate and nervonic acid salt of NR.

IR (KBr) $v_{max}$3415, 2924, 1695, 1465, 1418, 1290, 1098, 728, 674 cm⁻¹.

EXAMPLE 10

Preparation of a malate of NR with MCC as a carrier

Under the protection of nitrogen, 1 g of the malate of NR in Example 4 was added to 1 g of MCC, and a resulting mixture was ground at a low temperature for about 10 min until the mixture had a particle size of about 200 mesh to obtain 2 g of a mixture of malate of NR and MCC.

IR (KBr) $v_{max}$3425, 2930, 1688, 1644, 1513, 1395, 1095, 1018, 667 cm⁻¹.

EXAMPLE 11

Preparation of a malate of NR with MCC as a carrier

Under the protection of nitrogen, 1 g of the malate of NR in Example 3 was added to 1 g of MCC, and a resulting mixture was ground at a low temperature for about 10 min until the mixture had a particle size of about 200 mesh to obtain 2 g of a mixture of malate of NR and MCC.

IR (KBr) $v_{max}$3365, 2906, 1695, 1591, 1396, 1099, 675 cm⁻¹.

EXAMPLE 12

Preparation of a citrate of NR with MCC as a carrier

Under the protection of nitrogen, 1 g of the citrate of NR in Example 2 was added to 1 g of MCC, and a resulting mixture was ground at a low temperature for about 10 min until the mixture had a particle size of about 200 mesh to obtain 2 g of a mixture of citrate of NR and MCC.

R (KBr) $v_{max}$3437, 2927, 2378, 1740, 1698, 1641, 1513, 1398, 1111, 897, 671 cm$^{-1}$.

EXAMPLE 13

Preparation of a citrate of NR with MCC as a carrier

Under the protection of nitrogen, 1 g of the citrate of NR in Example 1 was added to 1 g of MCC, and a resulting mixture was ground at a low temperature for about 10 min until the mixture had a particle size of about 200 mesh to obtain 2 g of a mixture of citrate of NR and MCC.

IR (KBr) $v_{max}$ 3415, 2921, 2368, 1698, 1625, 1513, 1401, 1098, 894, 670, 619 cm$^{-1}$.

EXAMPLE 14

Preparation of a malate of NR with apple cider vinegar powder as a carrier

Under the protection of nitrogen, 1 g of the malate of NR in Example 4 was added to 1 g of apple cider vinegar powder (10%), and a resulting mixture was ground at a low temperature for about 10 min until the mixture had a particle size of about 200 mesh to obtain 2 g of a mixture of malate of NR and apple cider vinegar powder.

IR (KBr) $v_{max}$3406, 2930, 1692, 1584, 1408, 1092, 1028, 674 cm$^{-1}$.

COMPARATIVE EXAMPLE

Preparation of a chlorine salt of NR

Under the protection of nitrogen and at a temperature of −10° C. to −5° C., NR (0.0220 mol, 1 eq) was dissolved in 50 mL of methanol, then 10 g of a 17% hydrogen chloride-methanol solution was added dropwise, and a resulting mixture was stirred for dissolution; then 1 g of activated carbon was added, and a resulting mixture was further stirred for 1 h and filtered; a resulting filtrate was added to 150 ml of anhydrous MTBE, and a resulting mixture was further stirred for 30 min, filtered under the protection of nitrogen, rinsed with anhydrous diethyl ether, and dried at a temperature below −5° C. to obtain 8 g of a product.

The method in Example 10 was used to prepare a chlorine salt of NR with MCC as a carrier.

Characterization data:

HNMR(400 MHz,MeOD): 9.72 (s,1H), 9.44-9.46 (d,1H), 9.05-9.07 (d,1H), 8.29-8.33 (t,1H), 6.22-6.23 (d,1H), 4.45-4.47 (t,1H), 4.41-4.43 (q,1H), 4.31-4.33 (t,1H), 3.99-4.03 (d,1H), 3.84-3.88 (d,1H).

IR (KBr) $v_{max}$3336, 2935, 1687, 1616, 1400, 1100, 675 cm$^{-1}$.

Stability test

I. Preparation of samples

1. The products of Examples 1 to 4, Examples 10 to 13, and the comparative example were each dispensed into 13 bottles, each of 50 mg; and the bottles were filled with nitrogen and sealed. One of the bottles (initial sample) was first tested, and the remaining 12 bottles were divided into two groups (each with 6 bottles) and stored. The bottles in each group were numbered 1 to 6 according to a test sequence. The two groups of bottles were stored at 2° C. to 8° C. and −20° C., respectively; and one sample was tested every month.

2. The products of Examples 6 to 9 and Example 14 were each dispensed into 7 bottles, each of 50 mg; and the bottles were filled with nitrogen and sealed. One of the bottles (initial sample) was first tested, and the remaining 6 bottles were numbered 1 to 6 according to a test sequence and then stored at 2° C. to 8° C. One sample was tested every month.

II. Preparation of test sample solutions

One bottle of sample was taken at a time and prepared into a 5 mL or 10 mL solution using a 5 mL or 10 mL volumetric flask, and then the solution was filtered through a membrane to be ready for purity test by HPLC.

III. HPLC test

Mobile phase: isocratic elution: 5% water (0.1% formic acid)+95% methanol (0.1% formic acid)

Wavelength: 254 nm

Temperature and humidity: 23.0° C. and 54% RH

Sample dissolution: dissolution by methanol

Chromatographic column: ODS-2, 4.6 * 250 mm, 5 μm, and constant pressure: 12 Mpa to 13 Mpa Flow rate: 1.0 mL/min Injection volume: 5 μL Running time: ≥15 min IV.

$$\text{Decomposition rate} = $$
$$(\text{purity of initial sample} - \text{purity of sample 6})/\text{purity}$$
$$\text{of initial sample} \times 100\%$$

TABLE 1

(−20° C.)

| Time (month) | Example 1 | Example 2 | Example 3 | Example 4 | Comparative Example |
|---|---|---|---|---|---|
| 0 | 98.930 | 98.471 | 98.573 | 98.818 | 98.525 |
| 1 | 98.828 | 98.317 | 98.691 | 98.547 | 98.284 |
| 2 | 98.450 | 98.079 | 98.310 | 98.629 | 98.087 |
| 3 | 98.190 | 98.168 | 98.288 | 98.316 | 97.701 |
| 4 | 98.252 | 97.933 | 98.076 | 98.207 | 97.449 |
| 5 | 97.978 | 97.806 | 97.912 | 98.081 | 97.575 |
| 6 | 97.814 | 97.788 | 97.645 | 98.100 | 97.210 |
| Decomposition rate | 1.13% | 0.69% | 0.94% | 0.73% | 1.33% |

TABLE 2

(2° C. to 8° C.)

| Time (month) | Example 1 | Example 2 | Example 3 | Example 4 | Comparative Example |
|---|---|---|---|---|---|
| 0 | 98.930 | 98.471 | 98.573 | 98.818 | 98.525 |
| 1 | 98.198 | 98.492 | 98.482 | 98.424 | 98.171 |
| 2 | 98.409 | 98.240 | 98.185 | 98.360 | 98.206 |
| 3 | 98.171 | 98.097 | 98.270 | 98.298 | 97.540 |
| 4 | 97.957 | 97.626 | 97.946 | 98.239 | 97.612 |
| 5 | 97.823 | 97.704 | 97.592 | 97.707 | 97.384 |
| 6 | 97.670 | 97.498 | 97.337 | 97.816 | 97.109 |
| Decomposition rate | 1.27% | 0.99% | 1.25% | 1.01% | 1.44% |

It can be seen from Table 1 and Table 2 that the lower the temperature, the better the stability of the salt of NR; and the malate and citrate of NR (in a molar ratio of either 1:1 or 1:2) are both better than the chlorine salt of NR (comparative example), this is because malic acid or citric acid can form an intimate ion pair with NR, which leads to some hydrophobicity and thus improves the stability.

From the comparison of Example 1 with Example 2 and Example 3 with Example 4, it is found that the molar ratio (NR to organic acid) of 1:2 leads to higher stability than the molar ratio (NR to organic acid) of 1:1. In a molar ratio of 1:1, NR and an organic acid are preferably present in the form of an ion pair according to the electron effect. When NR and an organic acid are fed in a molar ratio of 1:2, according to HNMR, it is found that one molecule of the NR and two molecules of the organic acid can exist stably. One molecule of the organic acid forms an ion pair with the NR, and then the other molecule of the organic acid forms a hydrogen bond with basic amide in the NR due to acid-base interaction, thereby achieving acid-base pairing, which helps to improve the stability of the salt. In addition, the two molecules of acid can provide a strongly acidic environment, and the stronger the acidity, the higher the stability of NR. For example, the acidity of NMN is stronger than that of NR, and thus the stability of NMN is much higher than that of NR. Furthermore, when NR and an organic acid are present in a molar ratio of 1:2, an NR content decreases, the influence of free hydroxyl and amide functional groups among molecules is weakened, and the stability increases.

TABLE 3

(2° C. to 8° C.)

| Time (month) | Example 6 | Example 7 | Example 8 | Example 9 | Example 14 |
|---|---|---|---|---|---|
| 0 | 58.585 | 97.487 | 91.719 | 97.812 | 97.086 |
| 1 | 58.918 | 96.170 | 90.593 | 96.397 | 95.776 |
| 2 | 58.755 | 96.818 | 92.279 | 97.108 | 96.931 |
| 3 | 59.925 | 96.836 | 91.762 | 96.870 | 96.510 |
| 4 | 57.507 | 96.504 | 90.745 | 96.607 | 96.208 |
| 5 | 58.363 | 96.701 | 90.329 | 95.914 | 96.350 |
| 6 | 57.150 | 95.257 | 90.140 | 95.128 | 95.601 |
| Decomposition rate | 2.45% | 2.29% | 1.72% | 2.74% | 1.53% |

After an organic acid salt of NR is compounded with another organic acid or apple cider vinegar powder, the stability is reduced, but still acceptable. Therefore, the addition of an organic acid or apple cider vinegar powder as a carrier does not significantly affect the stability of the organic acid salt of NR. After an organic acid or apple cider vinegar powder is compounded with NR to form a composite nutritional additive, the components can be complementary and coordinated to produce a superimposed effect, which has potential application value.

TABLE 4

(−20° C.)

| Time (month) | Example 10 | Example 11 | Example 12 | Example 13 | Comparative Example |
|---|---|---|---|---|---|
| 0 | 98.759 | 98.550 | 98.316 | 98.694 | 97.917 |
| 1 | 98.632 | 98.180 | 98.440 | 98.633 | 97.874 |
| 2 | 98.714 | 98.442 | 98.259 | 98.441 | 97.656 |
| 3 | 98.557 | 98.395 | 98.213 | 98.527 | 97.326 |
| 4 | 98.324 | 98.308 | 98.007 | 98.372 | 97.470 |
| 5 | 98.491 | 98.273 | 98.110 | 98.393 | 97.319 |
| 6 | 98.425 | 98.112 | 98.041 | 98.238 | 97.277 |
| Decomposition rate | 0.34% | 0.45% | 0.28% | 0.46% | 0.65% |

TABLE 5

(2° C. to 8° C.)

| Time (month) | Example 10 | Example 11 | Example 12 | Example 13 | Comparative Example |
|---|---|---|---|---|---|
| 0 | 98.759 | 98.550 | 98.316 | 98.694 | 97.917 |
| 1 | 98.691 | 98.339 | 98.282 | 98.625 | 97.776 |
| 2 | 98.506 | 98.031 | 98.326 | 98.458 | 98.015 |

TABLE 5-continued (2° C. to 8° C.)

| Time (month) | Example 10 | Example 11 | Example 12 | Example 13 | Comparative Example |
|---|---|---|---|---|---|
| 3 | 98.239 | 98.274 | 98.028 | 98.083 | 97.693 |
| 4 | 98.317 | 97.932 | 97.805 | 98.121 | 97.542 |
| 5 | 98.342 | 97.786 | 97.734 | 97.833 | 97.380 |
| 6 | 98.251 | 97.875 | 97.782 | 98.017 | 97.154 |
| Decomposition rate | 0.51% | 0.68% | 0.54% | 0.69% | 0.78% |

After an organic acid salt of NR is compounded with MCC, the organic acid salt of NR with MCC as a carrier exhibits higher stability (comparison of Examples 10 to 13 with Examples 1 to 4). This is because MCC has hydrophobicity and heat resistance, which can prevent moisture penetration. When MCC is added, the molar ratio (NR to organic acid) of 1:2 (Examples 10 and 12) leads to higher stability than the molar ratio (NR to organic acid) of 1:1 (Examples 11 and 13). The malate or citrate of NR compounded with MCC exhibits higher stability than the corresponding chloride salt of NR compounded with MCC (comparative example), which further supports the previous conclusion.

The above described are merely specific implementations of the present disclosure, and the protection scope of the present disclosure is not limited thereto. Any modification or replacement easily conceived by those skilled in the art within the technical scope of the present disclosure should fall within the protection scope of the present disclosure. Therefore, the protection scope of the present disclosure should be subject to the protection scope of the claims.

What is claimed is:

1. An organic acid salt of nicotinamide riboside (NR), wherein an organic acid is citric acid or malic acid; a molar ratio of the NR to the organic acid is 1:2.

2. A preparation method of the organic acid salt of NR according to claim 1, comprising: under a protection of nitrogen, dissolving the NR in methanol, adding the organic acid to obtain a first resulting mixture, and stirring the first resulting mixture; adding methyl tert-butyl ether (MTBE) or ethyl acetate to obtain a second resulting mixture, and further stirring the second resulting mixture; and filtering, washing, and drying to obtain a product.

3. A composition of the organic acid salt of NR, comprising the organic acid salt of NR and a carrier, wherein the carrier is selected from the group consisting of malic acid, tannic acid, eicosapentaenoic acid (EPA), docosahexaenoic acid (DHA), caffeic acid, trans-cinnamic acid, trans-4-hydroxy-cinnamic acid, lactic acid, monosodium citrate, disodium citrate, citric acid, chlorogenic acid, gluconic acid, ferulic acid, royal jelly acid, nervonic acid, chicoric acid, rosmarinic acid, carnosic acid, niacin, adipic acid, lauric acid, monopotassium glycyrrhizinate (MPG), folic acid, chondroitin sulfate (CS), potassium hydrogen tartrate, salicylic acid, glycine, glutamic acid, alanine, arginine, leucine, isoleucine, valine, cystine, cysteine, methionine, threonine, serine, phenylalanine, tyrosine, tryptophan, proline, hydroxyproline, and aspartic acid; and the organic acid salt is the organic acid salt according to claim 1.

4. The composition of the organic acid salt of NR according to claim 3, wherein the carrier is selected from the group consisting of niacin, glutamic acid, royal jelly acid, and nervonic acid, and the organic acid salt is a malate of NR.

5. A composition of the organic acid salt of NR, comprising the organic acid salt of NR and a carrier, wherein the carrier is selected from the group consisting of microcrystalline cellulose (MCC) and apple cider vinegar powder; and the organic acid salt is the organic acid salt according to claim 1.

6. A preparation method of the composition according to claim 3, comprising: under a protection of nitrogen, mixing and grinding the organic acid salt of NR and the carrier.

7. The preparation method of the composition according to 6, wherein the carrier is selected from the group consisting of niacin, glutamic acid, royal jelly acid, and nervonic acid, and the organic acid salt is a malate of NR.

8. A preparation method of the composition according to 5, comprising: under a protection of nitrogen, mixing and grinding the organic acid salt of NR and the carrier.

* * * * *